US012606595B2

(12) United States Patent
Kim et al.

(10) Patent No.: US 12,606,595 B2
(45) Date of Patent: *Apr. 21, 2026

(54) REGENTIDE-041 AND COMPOSITION COMPRISING REGENTIDE-041 FOR IMPROVING SKIN CONDITION

(71) Applicant: NINEBIOPHARM CO., LTD., Cheongju-si (KR)

(72) Inventors: Jae Hwan Kim, Sejong-si (KR); Ji Heon Rhim, Sejong-si (KR); Hye In Ahn, Cheongju-si (KR); Ri Ra Lee, Gwangju-si (KR); Hae Yeong Kang, Cheongju-si (KR)

(73) Assignee: NINEBIOPHARM CO., LTD., Cheongju-si (KR)

( * ) Notice: Subject to any disclaimer, the term of this patent is extended or adjusted under 35 U.S.C. 154(b) by 670 days.

This patent is subject to a terminal disclaimer.

(21) Appl. No.: 17/997,801

(22) PCT Filed: Jun. 8, 2021

(86) PCT No.: PCT/KR2021/007159
§ 371 (c)(1),
(2) Date: Nov. 2, 2022

(87) PCT Pub. No.: WO2021/251727
PCT Pub. Date: Dec. 16, 2021

(65) Prior Publication Data
US 2023/0159590 A1      May 25, 2023

(30) Foreign Application Priority Data
Jun. 8, 2020   (KR) ........................ 10-2020-0068975

(51) Int. Cl.
| | |
|---|---|
| *C07K 7/08* | (2006.01) |
| *A61K 8/64* | (2006.01) |
| *A61K 38/00* | (2006.01) |
| *A61L 27/22* | (2006.01) |
| *A61P 17/02* | (2006.01) |
| *A61Q 19/08* | (2006.01) |

(52) U.S. Cl.
CPC .................. *C07K 7/08* (2013.01); *A61K 8/64* (2013.01); *A61L 27/227* (2013.01); *A61P 17/02* (2018.01); *A61Q 19/08* (2013.01); *A61K*
*38/00* (2013.01); *A61L 2400/06* (2013.01); *A61L 2430/34* (2013.01)

(58) Field of Classification Search
None
See application file for complete search history.

(56) References Cited

U.S. PATENT DOCUMENTS

2023/0210748 A1 * 7/2023 Kim ........................ A61Q 19/08
424/59

FOREIGN PATENT DOCUMENTS

| | | | | |
|---|---|---|---|---|
| CN | 108991532 A | 12/2018 | | |
| KR | 20130055505 A | 5/2013 | | |
| KR | 20200057588 A | 5/2020 | | |
| KR | 20200057589 A | 5/2020 | | |
| WO | WO-2018044234 A1 * | 3/2018 | ........... | C07K 14/811 |

OTHER PUBLICATIONS

Loo et al. "Identification and Characterization of Roseltide, a Knottin-type Neutrophil Elastase Inhibitor Derived from Hibiscus sabdariffa" Sci Rep. 6:39401. (Year: 2016).*
Genbank accession No. AKJ29743.1 (2015).
Loo et al., "Identification and Characterization of Roseltide, a Knottin-type Neutrophil Elastase Inhibitor Derived from Hibiscus sabdariffa," Scientific Reports, 6:39401 (2016).

* cited by examiner

*Primary Examiner* — Sudhakar Katakam
*Assistant Examiner* — Zachary J Miknis
(74) *Attorney, Agent, or Firm* — MEDLER FERRO WOODHOUSE & MILLS PLLC

(57)          ABSTRACT

The present invention relates to Regentide-041 and, more specifically, to a use of Regentide-041 for improving skin conditions. Regentide-041 according to the present invention is free of cytotoxicity and has remarkable effects of skin aging reduction, skin regeneration, skin elasticity improvement, skin wrinkle prevention, skin wrinkle reduction, and skin wound recovery and as such, can be variously utilized in the pharmaceutical, medicinal, cosmetic, and food fields.

5 Claims, 7 Drawing Sheets
Specification includes a Sequence Listing.

[48hr, Human skin keratinocyte]

[48hr, Human skin dermal fibroblast]

[0~8days, Human skin keratinocyte]

(Human skin keratinocyte)

[Human skin dermal fibroblast]

REGENTIDE-041 AND COMPOSITION COMPRISING REGENTIDE-041 FOR IMPROVING SKIN CONDITION

TECHNICAL FIELD

The present invention relates to Regentide-041, and more particularly, to a use of Regentide-041 for improving skin conditions.

BACKGROUND ART

The skin is largely divided into epidermis, dermis, and subcutaneous tissue. The dermis contains important appendages of the skin, such as blood vessels, lymphatic system, pores, and fibroblasts, and it is a thick layer that is 15 to 40 times the thickness of the epidermis and occupies most of the skin. The dermal tissue consists of collagen which is a crosslinked fiber, and elastin which is an elastic fiber, and these are synthesized in fibroblasts. Collagen is a long fiber and plays a role of making the body support, bonding, and interface. Collagen plays a role of resisting pressure or external forces applied to the skin. On the other hand, elastin plays a role of maintaining the elasticity of the skin like a spring. Collagen and elastin form a mesh structure to maintain the elasticity of the skin.

As the skin ages, wrinkles appear, and the number, depth, and range thereof increase with age. Aging is divided into intrinsic and extrinsic aging, and intrinsic aging is a continuous decline in the structure and physiological functions of the skin with age. Aging caused by external factors appears due to causes such as exposure to ultraviolet rays over a long period of time.

It has been reported that elastase produced from fibroblasts plays an important role in the three-dimensional distortion of skin elastic fibers, and the increase in elastase activity contributes to the formation of skin wrinkles by reducing elastin and collagen of the skin. Since the activity of elastase increases after UV irradiation, it is known that the change in the activity of elastase is the main cause of the decrease in skin elasticity and the creation of wrinkles due to UV rays.

DISCLOSURE

Technical Problem

Accordingly, the present inventors have completed the present invention by developing a peptide Regentide-041 while searching for a novel skin improvement material, and confirming its skin improvement effect.

Accordingly, an object of the present invention is to provide a peptide represented by the amino acid sequence of SEQ ID NO: 1 and a composition for improving skin conditions including the same.

Another object of the present invention is to provide a method for treating a wound, including a step of administering a peptide represented by the amino acid sequence of SEQ ID NO: 1 to an individual in need thereof.

Technical Solution

In order to achieve the above objects, the present invention provides a peptide represented by the amino acid sequence of SEQ ID NO: 1.

The present invention also provides a cosmetic composition for improving skin conditions, including the peptide.

The present invention also provides a quasi-drug composition for improving skin conditions, including the peptide.

The present invention also provides a food composition for improving skin conditions, including the peptide.

The present invention also provides a health functional food composition for improving skin conditions, including the peptide.

The present invention also provides a filler composition for improving skin conditions, including the peptide.

The present invention also provides a filler for skin injection including the peptide.

The present invention also provides a pharmaceutical composition for wound treatment including the peptide.

The present invention also provides a method for treating a wound, including the step of administering the peptide to an individual in need thereof

Advantageous Effects

Regentide-041 according to the present invention not only has no cytotoxicity, but also has remarkable skin aging improvement, skin regeneration, skin elasticity improvement, skin wrinkle prevention, skin wrinkle improvement and skin wound regeneration effects, and thus it can be variously used in pharmaceutical, medicine, cosmetic, and food fields.

BEST MODE FOR CARRYING OUT THE INVENTION

Figure 1:
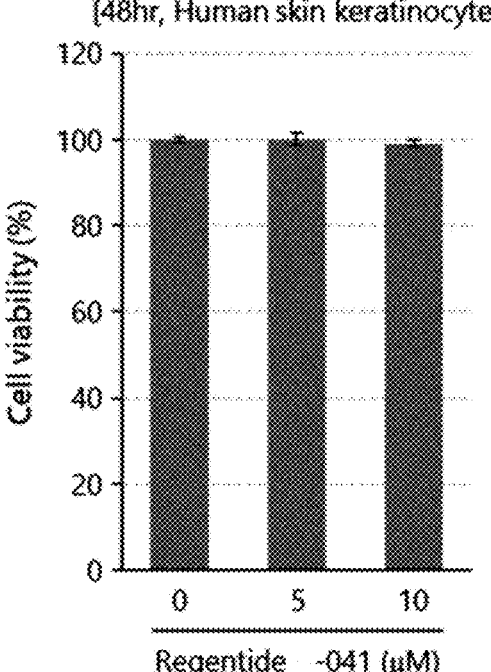
FIG. 1 is a view showing the results of evaluating the cytotoxicity of Regentide-041 according to the present invention to epidermal keratinocytes and fibroblasts.
Figure 1:
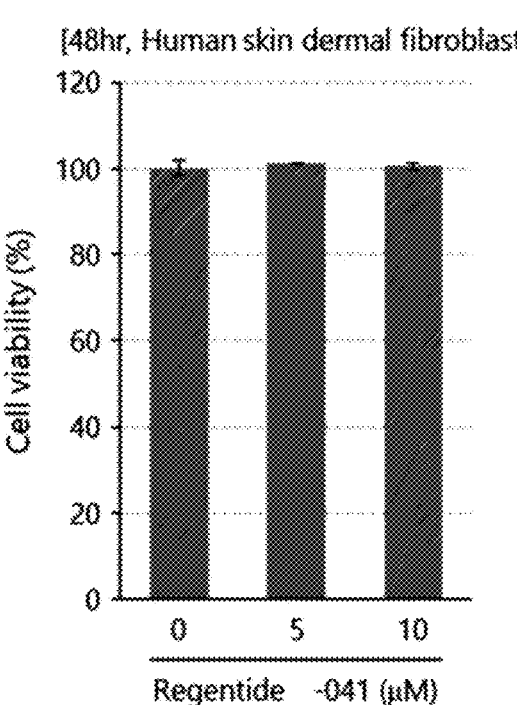

Hereinafter, the present invention will be described in detail.

According to an aspect of the present invention, the present invention provides a peptide represented by the amino acid sequence of SEQ ID NO: 1.

In the present invention, a peptide refers to a linear molecule formed by combining amino acid residues with each other by peptide bonds. The peptide may be prepared according to a chemical synthesis method known in the art, and preferably may be prepared according to a solid-phase synthesis technique, but is not limited thereto.

In an embodiment of the present invention, the peptide represented by the amino acid sequence of SEQ ID NO: 1 is preferably one in which an amine group (—NH₂) is conjugated to the C-terminus, and the amine group-conjugated peptide was named as 'Regentide-041'. Regentide-041 may be represented by the amino acid of SEQ ID NO: 2. Regentide-041 is one in which an amine group is conjugated to the C-terminus of the peptide represented by the amino acid sequence of SEQ ID NO: 1, and stability within the tissue may be remarkably improved.

In an embodiment of the present invention, it was confirmed through an experiment that the peptide represented by the amino acid sequence of SEQ ID NO: 1 has no cytotoxicity to epidermal keratinocytes and fibroblasts, and has remarkable cell proliferation promotion, collagen synthesis promotion and cell migration promotion effects.

The scope of the present invention includes functional equivalents of the peptide represented by the amino acid sequence of SEQ ID NO: 1.

In the present invention, the functional equivalents include ones having a sequence homology (i.e., identity) of at least 80%, preferably 90%, more preferably 95% or more with the amino acid sequence represented by SEQ ID NO: 1 as a result of addition, substitution, or deletion of amino acid, for example, ones having a sequence homology of 80%, 81%, 82%, 83%, 84%, 85%, 86%, 87%, 88%, 89%, 90%, 91%, 92%, 93%, 94%, 95%, 96%, 97%, 98%, 99%, and 100%, and refer to peptides that exhibit substantially the same bioactivity as the peptide represented by the amino acid sequence of SEQ ID NO: 1. In addition, in the peptide represented by the amino acid sequence of SEQ ID NO: 1 according to the present invention, not only a protein having its native amino acid sequence, but also amino acid sequence variants thereof are included in the scope of the present invention. The variant of the peptide represented by the amino acid sequence of SEQ ID NO: 1 refers to a peptide in which the native amino acid sequence of the peptide and one or more amino acid residues have different sequences by deletion, insertion, non-conservative or conservative substitution, or a combination thereof. Amino acid exchanges in proteins and peptides that do not entirely alter the activity of the molecule are known in the art. The peptide represented by the amino acid sequence of SEQ ID NO: 1 or a variant thereof may be extracted or synthesized from nature, or prepared by a DNA sequence-based genetic recombination method.

Further, the sequence homology may be determined by a general standard method used to compare similar portions of the amino acid sequences constituting the peptide. A computer program such as BLAST or FASTA aligns amino acids making up each of two or more proteins so that the amino acids are optimally matched (either along the full length of one or both sequences, or along the predicted portions of one or both sequences). The program provides a default opening penalty and a default gap penalty and provides a scoring matrix such as PAM250 (standard scoring matrix) that may be used in conjunction with a computer program. For example, sequence homology expressed as a percentage may be calculated as follows: obtaining a value by multiplying the total number of matched sequences (identical matches) by 100, and then dividing the value by the sum of the length of the longer sequence in the corresponding span (matched span) and the number of gaps introduced into the longer sequence to align the two sequences.

In the present invention, substantially the same bioactivity means skin condition improvement activity, and more specifically, means one or more kinds of activities selected from the group consisting of skin aging improvement, skin regeneration, skin elasticity improvement, skin wrinkle prevention, skin wrinkle improvement, and skin wound regeneration.

Further, the scope of the functional equivalents includes derivatives in which some chemical structures of amino acids made up while maintaining the basic skeleton and skin condition improvement activity of the peptide represented by the amino acid sequence of SEQ ID NO: 1 are modified. For example, structural modifications to alter the stability, storage, volatility or solubility of the protein are included therein.

According to another aspect of the present invention, the present invention provides a composition for improving skin conditions, including a peptide represented by the amino acid sequence of SEQ ID NO: 1.

In an embodiment of the present invention, the peptide is preferably one in which an amine group is conjugated to the C-terminus, and this may be one represented by the amino acid sequence of SEQ ID NO: 2.

In the present invention, "improvement" refers to a parameter related to alleviation or treatment of a condition, for example, all acts that at least reduce the severity of a symptom.

"Improving skin conditions" according to the present invention may be one or more kinds of activities selected from the group consisting of skin aging improvement, skin regeneration, skin elasticity improvement, skin wrinkle prevention, skin wrinkle improvement, and skin wound regeneration.

In the present invention, "skin aging" refers to all diseases caused by an increase in active oxygen, and nonlimiting examples of the skin aging may include wrinkles, sagging skin, reduced elasticity, and the like. In the present invention, "skin regeneration", "skin elasticity improvement" or "skin wrinkle prevention or improvement" refers to all actions that increase the total amount of collagen by inhibiting collagenase activity.

In the present invention, "skin wound regeneration" refers to all actions that regenerate damaged skin due to cut wounds, etc. by increasing the number of skin cells and promoting skin cell migration ability.

In an embodiment of the present invention, the skin aging is photoaging or natural aging, but the scope of the present invention is not limited by the cause of skin aging.

In an embodiment of the present invention, the peptide preferably has a concentration of 0.1 to 1,000 μM.

In an embodiment of the present invention, the cosmetic composition is preferably formulated into a filler, but is not limited thereto.

The composition for improving skin conditions according to the present invention may be a cosmetic composition, a quasi-drug composition, a food composition, a health functional food composition, or a filler composition.

When the composition for improving skin conditions according to the present invention is a cosmetic composition, the cosmetic composition according to the present invention may further include, in addition to the active ingredients, conventional auxiliary agents such as antioxidants, stabilizers, solubilizers, vitamins, pigments, fragrances, etc. commonly used in cosmetic compositions, and carriers. For example, the cosmetic composition may further include auxiliary components such as glycerin, butylene glycol, polyoxyethylene hydrogenated castor oil, tocopheryl acetate, citric acid, panthenol, squalane, sodium citrate, and allantoin.

Since the cosmetic composition according to the present invention basically acts on the skin, it may be prepared in any formulation conventionally prepared with reference to a cosmetic composition in the art. For example, the cosmetic composition according to the present invention may be formulated as solutions, suspensions, emulsions, pastes, gels, creams, lotions, powders, soaps, surfactant-containing cleansings, oils, powder foundations, emulsion foundations, wax foundations, sprays, etc., but is not limited thereto. More specifically, it may be prepared in a formulation of a soft lotion, a nourishing lotion, a nourishing cream, a massage cream, an essence, an eye cream, a cleansing cream, a cleansing foam, a cleansing water, a mask pack, a spray, or a powder.

When the formulation of the present invention is a paste, cream, or gel, animal oil, vegetable oil, wax, paraffin, starch, tracanth, cellulose derivatives, polyethylene glycol, silicone, bentonite, silica, talc, zinc oxide, etc. may be included as carrier components.

When the formulation of the present invention is a powder or spray, lactose, talc, silica, aluminum hydroxide, calcium silicate, polyamide powder, etc. may be included as carrier components, and particularly, when it is a spray, propellants such as chlorofluorohydrocarbon, propane/butane, and dimethyl ether may be further included.

When the formulation of the present invention is a solution or emulsion, a solvent, solubilizer, emulsifier, etc. may be included as carrier components, and specifically, water, ethanol, isopropanol, ethyl carbonate, ethyl acetate, benzyl alcohol, benzyl benzoate, propylene glycol, 1,3-butylglycol oil, glycerol aliphatic ester, polyethylene glycol, fatty acid ester of sorbitan, and the like may be included.

When the formulation of the present invention is a suspension, carrier components may include: a liquid diluent such as water, ethanol, propylene glycol, or the like; a suspending agent such as ethoxylated isostearyl alcohol, polyoxyethylene sorbitol ester, polyoxyethylene sorbitan ester, or the like; microcrystalline cellulose, aluminum metahydroxide, bentonite, agar, tracanth, and the like.

When the formulation of the present invention is a surfactant-containing cleansing, the carrier components may include aliphatic alcohol sulfate, aliphatic alcohol ether sulfate, sulfosuccinic acid monoester, isethionate, imidazolinium derivatives, methyl taurate, sarcosinate, fatty acid amide ether sulfate, alkylamidobetaine, aliphatic alcohol, fatty acid glyceride, fatty acid diethanolamide, vegetable oil, lanolin derivatives, ethoxylated glycerol fatty acid ester, and the like.

The composition for improving skin conditions according to the present invention may be a quasi-drug composition.

In the present invention, quasi-drugs refer to articles with a milder action than drugs among articles used for the purpose of diagnosing, treating, improving, alleviating, treating or preventing diseases of humans or animals. For example, according to the Pharmaceutical Affairs Act, quasi-drugs are ones excluding articles used for the purpose of drugs, and include products used for the treatment or prevention of diseases in humans and animals, products with minor or no direct action on the human body, and the like.

The quasi-drug composition according to the present invention may be prepared in the form of one selected from the group consisting of a body cleanser, a foam, a soap, a mask, an ointment, a cream, a lotion, an essence, and a spray, but is not limited thereto.

In the quasi-drug composition according to the present invention, the description of the peptide represented by the amino acid sequence of SEQ ID NO: 1 and the descriptions of skin regeneration, skin elasticity improvement, skin wrinkle prevention or improvement, skin aging prevention or improvement, skin inflammation improvement, and skin whitening improvement are the same as those described above with respect to the cosmetic composition.

The food composition for improving skin conditions according to the present invention may be used as a health functional food, food additive, or dietary supplement.

When the peptide represented by the amino acid sequence of SEQ ID NO: 1 is used as a food additive, the mixture may be appropriately used according to a conventional method such as being added as it is, or mixed and used with other foods or food ingredients.

Further, it is of course that the mixing amount of the peptide represented by the amino acid sequence of SEQ ID NO: 1 may be suitably changed depending on the purpose of use (prevention, health or therapeutic treatment), it is preferable that the peptide is contained in an amount of 0.01 to 95% by weight based on the total weight of the food composition, and it is more preferable that it is contained in an amount of 1 to 80% by weight. When the content is less than 0.01% by weight, the antioxidant or anti-inflammatory effect may be insignificant, and when it exceeds 95% by weight, the effect increase rate is low compared to the amount used, and thus it may be uneconomical.

As a specific example, when manufacturing food or beverage, the peptide represented by the amino acid sequence of SEQ ID NO: 1 according to the present invention is added in an amount of 15% by weight or less, preferably 10% by weight or less with respect to the raw material. However, when consumed for a long period of time for the purposes of health and hygiene or health control, it may be added in an amount not more than the above range, and since there is no problem in terms of safety, the active ingredient may also be used in an amount not less than the above range.

There is no particular limitation on the type of the food, but examples of the food to which the peptide represented by the amino acid sequence of SEQ ID NO: 1 according to the present invention may be added may include meat, sausage, bread, chocolate, candy, snacks, confectionery, pizza, ramen, other noodles, gums, dairy products including ice cream, various soups, beverages, teas, drinks, alcoholic beverages, vitamin complexes, etc., and include all health foods in the ordinary sense.

When the food composition according to the present invention is prepared as a beverage, it may include additional ingredients such as various flavoring agents or natural carbohydrates like conventional beverages. Examples of the natural carbohydrate may include monosaccharides such as glucose and fructose; disaccharides such as maltose and sucrose; natural sweeteners such as dextrin and cyclodextrin; synthetic sweeteners such as saccharin and aspartame; and the like. The natural carbohydrate is included in an amount of 0.01 to 10% by weight, preferably 0.01 to 0.1% by weight, based on the total weight of the food composition according to the present invention.

The food composition according to the present invention may include various nutrients, vitamins, electrolytes, flavoring agents, coloring agents, pectic acid and salts thereof, alginic acid and salts thereof, organic acids, protective colloidal thickeners, pH adjusters, stabilizers, preservatives, a carbonation agent used in glycerin, alcohol, and carbonic acid beverages, etc., and may include fruit flesh for the production of natural fruit juice, fruit juice beverages, and vegetable beverages, but is not limited to. These components may be used independently or in combination. Although the ratios of the additives are not particularly limited, they are preferably contained within the amount range of 0.01 to 0.1% by weight based on the total weight of the food composition according to the present invention.

In the case of long-term ingestion for health and hygiene purposes or for health control purpose, the food composition according to the present invention may be taken for a long time since there is no problem in terms of safety.

The composition for improving skin conditions according to the present invention may be a filler composition.

In the present invention, a filler refers to an injectable material replenishing skin tissue such as improvement of wrinkles, and restoration of aesthetic volume, by injecting a biocompatible material intradermally or subcutaneously. Recently, fillers include not only substances similar to the skin, but also substances that promote the proliferation of cells within the skin, substances that promote the production of collagen etc. When you receive filler treatment, such effects as smoothening out of wrinkles in a short time, thickening of thin lips, and filling of pitted scars are exhibited. Currently, as a material for manufacturing a filler approved by FDA or MFDS, there are collagen, hyaluronic acid, calcium hydroxylapatite, polylactic acid, and the like.

Further, the filler composition according to the present invention may be formulated in a powder form, more specifically in a freeze-dried powder form, in order to provide use convenience and storage stability. Meanwhile, the filler composition needs a pretreatment step of dissolving it in an aqueous medium such as PBS to solubilize it before injection into the skin, but direct application of the solutionized filler composition is also possible depending on storage and formulation conditions.

In an embodiment of the present invention, the filler composition according to the present invention may further include a cell growth factor or a vitamin in order to impart an effective skin regeneration effect. The cell growth factor is a generic term for polypeptides that promote division, growth, and differentiation of cells, and may be preferably selected from the group consisting of fibroblast growth factor (FGF), epidermal growth factor (EGF), keratinocyte growth factor (KGF), transforming growth factor-alpha (TGF-α), transforming growth factor-beta (TGF-(β), granulocyte colony stimulating factor (GCSF), insulin-like growth factor (IGF), vascular endothelial growth factor (VEGF), hepatocyte growth factor (HGF), platelet-derived growth factor-BB (PDGFBB), brain-derived neurotrophic factor (BDNF), and glial cell line-derived neurotrophic factor (GDNF), in which the cell growth factor may be contained in a concentration of 20 ng/ml to 20 μg/ml, but is not limited thereto.

In order to relieve pain during the injection process, the filler composition according to the present invention may further include a local anesthetic. The local anesthetic may be selected from the group consisting of ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquine, dimethocaine, diferodone, dicyclonine, ecgonidine, ecgonine, ethyl chloride, etidocaine, beta-eucaine, euprocin, phenalkomine, formocaine, hexylcaine, hydroxytetracaine, isobutyl p-aminobenzoate, leucinocaine mesylate, reboxadrol, lidocaine, mepivacaine, meprylcaine, metabutoxycaine, methyl chloride, myrtecaine, naepaine, octacaine, orthocaine, oxethazine, parethoxycaine, phenacaine, phenol, piperocaine, piridocaine, polidocanol, pramoxine, prilocaine, procaine, propanocaine, proparacaine, propicocaine, propoxycaine, pseudococaine, pyrrocaine, ropivacaine, bupivacaine, salicyl alcohol, tetracaine, tolylcaine, trimecaine, zolamine, and salts thereof, and the anesthetic may be contained in an amount of preferably 0.1 to 5.0% by weight, more preferably 0.2 to 1.0% by weight, based on the total weight of the filler composition, but is not limited thereto.

In order to prevent oxidation and decomposition of the hydrogel gelated and produced in the body, the filler composition according to the present invention may further include an antioxidant. The antioxidant may be selected from the group consisting of polyol, mannitol, and sorbitol, and the antioxidant may be contained in an amount of preferably 0.1 to 5.0% by weight, more preferably 0.2 to 1.0% by weight, based on the total weight of the filler composition, but is not limited thereto.

According to another aspect of the present invention, the present invention provides a filler for skin injection including a peptide represented by the amino acid sequence of SEQ ID NO: 1.

In an embodiment of the present invention, the peptide preferably has an amine group conjugated to the C-terminus, and this may be represented by the amino acid sequence of SEQ ID NO: 2.

In an embodiment of the present invention, the filler is for improving skin conditions, which is preferably one or more kinds selected from the group consisting of skin aging improvement, skin regeneration, skin elasticity improvement, skin wrinkle prevention, skin wrinkle improvement, and skin wound regeneration, but is not limited thereto.

In an embodiment of the present invention, the filler is preferably for injection, but the scope of the present invention is not limited thereto.

According to another aspect of the present invention, the present invention provides a pharmaceutical composition for wound treatment including a peptide represented by the amino acid sequence of SEQ ID NO: 1.

In an embodiment of the present invention, the peptide preferably has an amine group conjugated to the C-terminus, and this may be represented by the amino acid sequence of SEQ ID NO: 2.

In the present invention, "wound treatment" refers to the action of treating the damaged site (i.e., wound) by increasing the number of cells and promoting cell migration ability in the damaged area due to a cut wound or the like.

The pharmaceutical composition for wound treatment according to the present invention may be formulated and used in various forms depending on conventional methods, respectively. For example, it may be formulated in oral dosage forms such as powders, granules, tablets, capsules, suspensions, emulsions, and syrups, and may be formulated and used in the form of external preparations, suppositories, and sterile injection solutions. However, it may be most preferable that the composition according to the present invention is provided in the form of an external preparation for skin. Specifically, it may be used in the form of a liquid, ointment, cream, lotion, spray, patch, gel or aerosol.

Further, it may further include a pharmaceutically acceptable carrier, an excipient and a diluent depending on each formulation. In addition, according to a conventional method, it may be formulated and used in the form of external preparations such as powders, granules, tablets, capsules, suspensions, emulsions, syrups, and aerosols, and sterile injection solutions, and may preferably have a formulation of cream, gel, patch, spray, ointment, oral preparation, lotion, liniment, paste, or cataplasmase. For example, in the case of an external skin preparation used locally in the corresponding site, it may include conventional additives, for example, a preservative, a solvent to assist drug penetration, and an emollient or the like in the case of ointments and creams, and may contain a conventional carrier such as ethanol or oleyl alcohol. Suitable preparations known in the art are preferably those disclosed in the literature (Remington's Pharmaceutical Science, recently Mack Publishing Company, Easton Pa.), but are not limited thereto.

The carrier, excipient and diluent include lactose, dextrose, sucrose, oligosaccharide, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, mineral oil, and the like. When preparing or formulating the pharmaceutical composition, it is prepared using a diluent or excipient such as a filler, an extender, a binder, a wetting agent, a disintegrant, and a surfactant usually used. Solid preparations for oral administration include tablets, pills, powders, granules, capsules, etc., and these solid preparations are prepared by mixing the composition with at least one excipient, for example, starch, calcium carbonate, sucrose, lactose, gelatin, etc. Further, in addition to simple excipients, lubricants such as magnesium stearate talc are also used. Liquid preparations for oral use correspond to suspensions, oral liquids, emulsions, syrups, and the like, and they may include various excipients such as wetting agents, sweeteners, flavoring agents, and preservatives in addition to water and liquid paraffin that are simple diluents frequently used. Preparations for parenteral administration include sterile aqueous solutions, non-aqueous solvents, suspending agents, emulsions, freeze-dried preparations, suppositories, and the like. The non-aqueous solvents and suspending agents may include propylene glycol, polyethylene glycol, vegetable oils such as olive oil, and injectable esters such as ethyl oleate. Witepsol, macrogol, tween 61, cacao butter, laurin butter, glycerogelatin, and the like may be used as the base of the suppository. The above-mentioned ingredients may be added independently or in combination to the active ingredients, that is, the pharmaceutical composition.

In the present invention, administration means providing the pharmaceutical composition according to the present invention to an individual by any appropriate method.

The pharmaceutical composition according to the present invention may be administered in an amount of an active ingredient or pharmaceutical composition inducing a biological or medical response in a tissue system, animal or human as considered by a researcher, veterinarian, doctor or other clinicians, that is, a therapeutically effective amount, which is an amount of inducing the relief of symptoms of the disease or disorder being treated. It is apparent to those skilled in the art that the therapeutically effective dosage and administration frequency for the pharmaceutical composition according to the present invention will vary depending on the desired effect. Therefore, the optimal dosage to be administered may be easily determined by those skilled in the art, and may be adjusted depending on various factors including the type of disease, the severity of the disease, the contents of active ingredients and other components contained in the composition, the type of formulation, the age, weight, and general health condition, sex, and diet of the patient, administration time, administration route, composition secretion rate, treatment period, and drugs used at the same time.

The pharmaceutical composition according to the present invention may be administered in an amount of 1 to 10,000 mg/kg/day, preferably 1 to 200 mg/kg/day, and may be administered once a day, or may be administered in several divided doses.

According to another aspect of the present invention, the present invention provides a method for treating a wound, the method including a step of treating a peptide represented by the amino acid sequence of SEQ ID NO: 1 on an individual in need thereof.

In an embodiment of the present invention, the individual may be an individual having a wound occurred; or an individual having the wound recovered, but is not limited thereto.

Duplicate content is omitted in consideration of the complexity of the present specification, and terms not defined otherwise in the present specification have the meanings commonly used in the art to which the present invention pertains.

MODE FOR CARRYING OUT THE INVENTION

Hereinafter, the present invention will be described in more detail through Examples. These Examples are only for illustrating the present invention, and it will be apparent to those of ordinary skill in the art that the scope of the present invention is not to be construed as being limited by these Examples.

Example 1. Peptide Synthesis

A peptide for skin protection and wrinkle improvement was synthesized. The synthesized peptide is represented by the amino acid sequence of SEQ ID NO: 1, and an amine group ($—NH_2$) was conjugated to the C-terminus of the peptide for the purpose of safety in the tissue. The peptide having the amine group conjugated to the C-terminus is represented by the amino acid sequence of SEQ ID NO: 2, and was named 'Regentide-041'.

TABLE 1

| Name | SEQ ID NO: | Amino acid sequence |
|---|---|---|
| Synthesized peptide | 1 | CIPRGGICLVAL |
| Regentide-041 | 2 | CIPRGGICLVAL-$NH_2$ |

Regentide-034 represented by the amino acid sequence of SEQ ID NO: 2 was used in the experiment to be described later.

Example 2. Cytotoxicity Evaluation of Regentide-041

The cytotoxicity of Regentide-041 prepared in Example 1 above was evaluated. Specifically, cytotoxicities were measured in HaCaT cells, which are human epidermal keratinocytes, and CCD-986Sk, which is human fibroblasts. Keratinocytes were dispensed at $3 \times 10^3$ cells/well and fibroblasts were dispensed at $5 \times 10^3$ cells/well in a 96-well plate, and then cultured in cell culture conditions for 24 hours in a medium containing 10% FBS. After culturing, 5 μM or 10 μM of Regentide-041 was added to an FBS-free medium, and this was cultured for 48 hours. Thereafter, 10 μl per well of CCK8 reaction solution (Dojindo Molecular Technologies, Kumamoto, Japan) was treated and reacted for 4 hours, and then absorbance was measured at 450 nm. The average absorbance value for each sample group was obtained, and the cell viability was evaluated by comparing it with the absorbance value of cells that had not been treated with Regentide-041 as a control group. The results of confirming the cytotoxicity of Regentide-041 are shown in FIG. 1.

As shown in FIG. 1, it was confirmed that Regentide-041 was not toxic to epidermal keratinocytes and fibroblasts.

Example 3. Cell Growth Promoting Efficacy of Regentide-041

3-1. Epidermal Keratinocyte Growth Promoting Efficacy

In order to confirm the cell proliferation ability of Regentide-041, HaCaT cells, which are epidermal keratinocytes, were dispensed at $1 \times 10^4$ cells/well in a 6-well plate, and then cultured in cell culture conditions for 6 hours in a medium containing 10% FBS. Thereafter, Regentide-041 was added at various concentrations (100, 200, and 500 nM) and cultured for 8 days. The medium containing 100, 200, or 500 nM of Regentide-041 was replaced every day, and the number of cells was measured at intervals of two days. The cell number measurement results are shown in FIG. 2.

Figure 2:
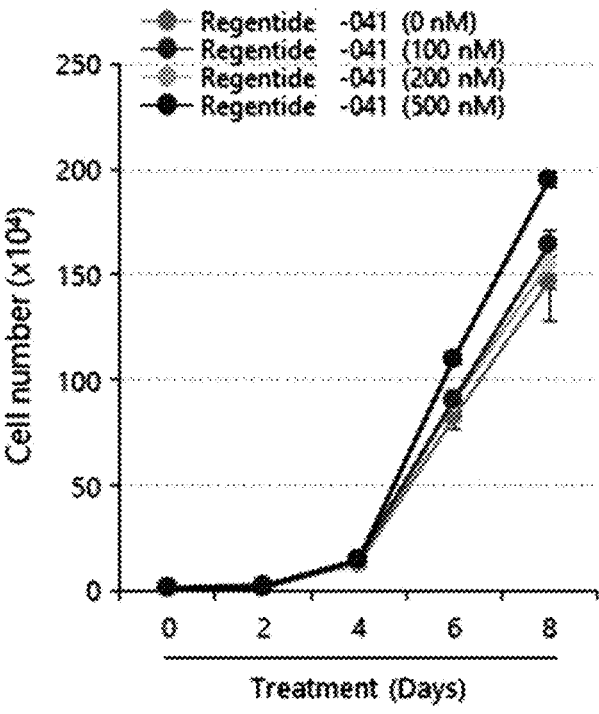
FIG. 2 is a view showing the results of confirming the growth promoting efficacy of the epidermal keratinocytes of Regentide-041 according to the present invention.
Figure 2:
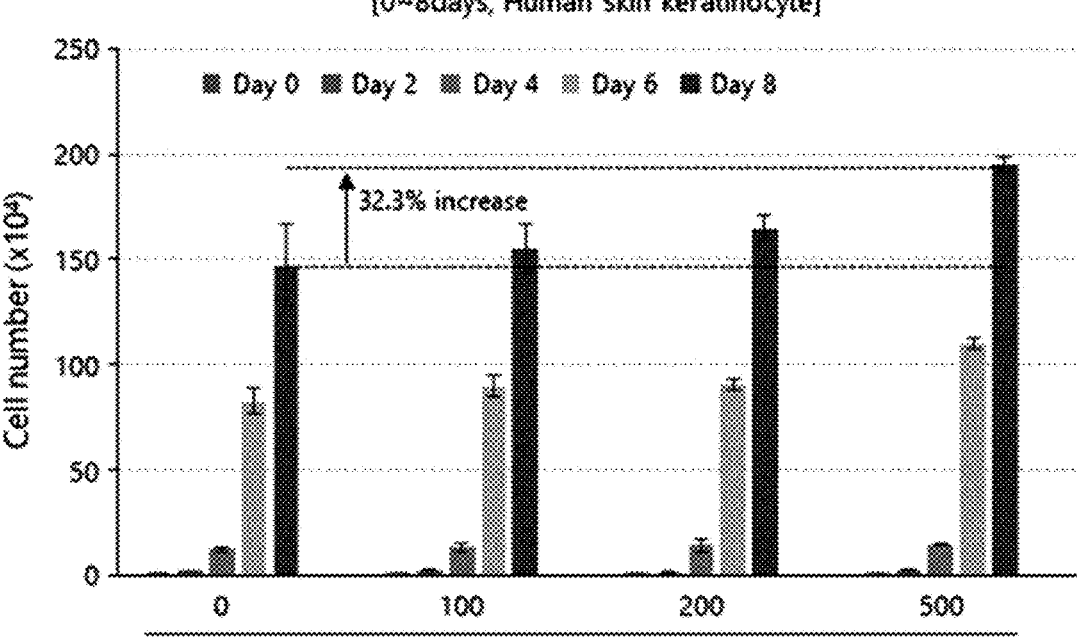

As shown in FIG. 2, it was confirmed that the Regentide-041 treatment group promoted the growth of epidermal keratinocytes in a concentration and time-dependent manner. Particularly, it was confirmed that the group treated with 500 nM of Regentide-041 after 8 days since it had been treated with Regentide-041 had a cell growth rate of about 32.3% higher than that of the control group that had not been treated with Regentide-041.

3-2. Fibroblast Growth Promoting Efficacy

In order to confirm the cell proliferation ability of Regentide-041, CCD986Sk cells, which are fibroblasts, were dispensed at $1 \times 10^4$ cells/well in a 6-well plate, and then cultured in cell culture conditions for 6 hours in a medium containing 10% FBS. Thereafter, Regentide-041 was added at various concentrations (100, 200, and 500 nM) and cultured for 8 days. The medium containing 100, 200, or 500 nM of Regentide-041 was replaced every day, and the number of cells was measured at intervals of two days. The cell number measurement results are shown in FIG. 3.

Figure 3:
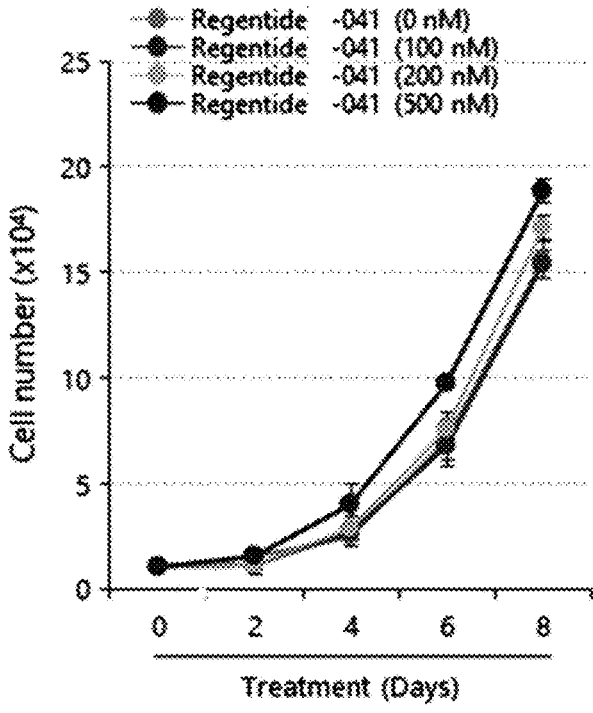
FIG. 3 is a view showing the results of confirming the growth promoting efficacy of the fibroblasts of Regentide-041 according to the present invention.
Figure 3:
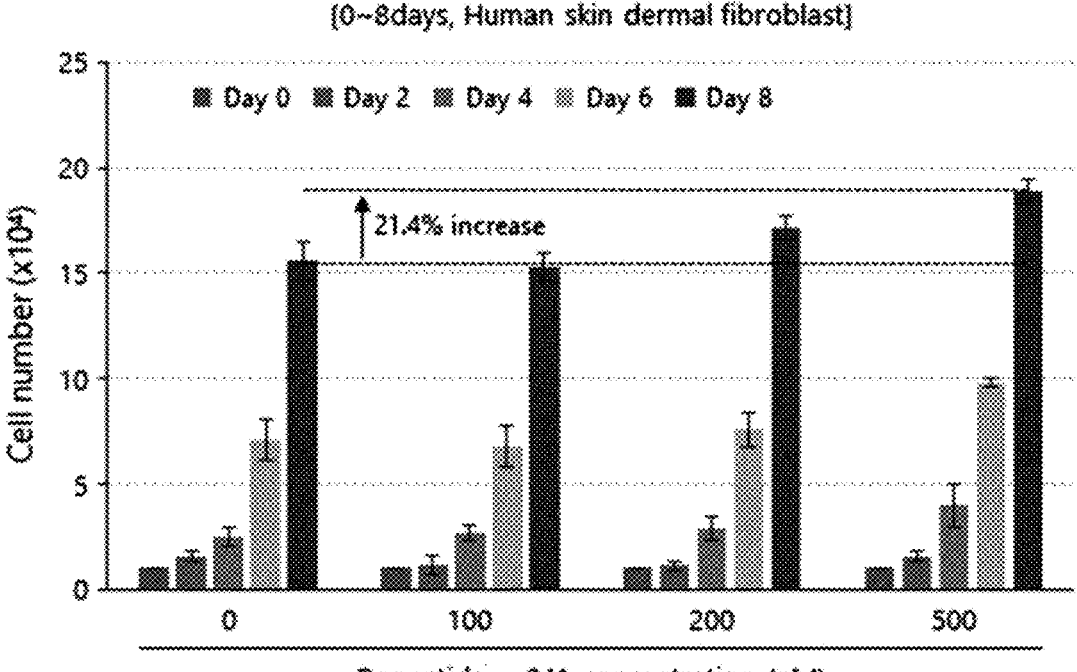

As shown in FIG. 3, it was confirmed that the Regentide-041 treatment group promoted the growth of fibroblasts in a concentration and time-dependent manner. It was confirmed that the group treated with 500 nM of Regentide-041 after 8 days since it had been treated with Regentide-041 had a cell growth rate of about 21.4% higher than that of the control group that had not been treated with Regentide-041.

Example 4. Confirmation of Elastin Synthesis Effect of Regentide-041

4-1. Elastase Activity Inhibitory Ability Analysis

In order to confirm the elastase activity inhibitory ability of Regentide-041, it was measured using the Neutrophil Elastase colorimetric method (BML-AK497-001, Enzo Life Science, Pennsylvania, USA). Specifically, after an assay buffer and D.W. were diluted at 1:1, an elastase reagent and a substrate reagent were diluted to have final concentrations of 2.2 μU/μl and 100 μM, respectively. In addition, Regentide-041 was diluted to have final concentrations of 0.1, 1, 10, 50, 100, and 150 μM, respectively. A working solution was prepared by mixing the assay buffer, elastase reagent, and Regentide-041 diluent. 95 μM of the working solution was put in each well of a 96-well plate and reacted at 37° C. for 5 minutes. Next, 5 μM of the substrate reagent was put, and absorbance was measured for 15 minutes at absorbance 405 nm with a Microplate reader (Epoch 2 Microplate spectrophotometer. Biotek, Winooski, VT, USA). The results of analyzing the elastase activities are shown in FIG. 4.

Figure 4:
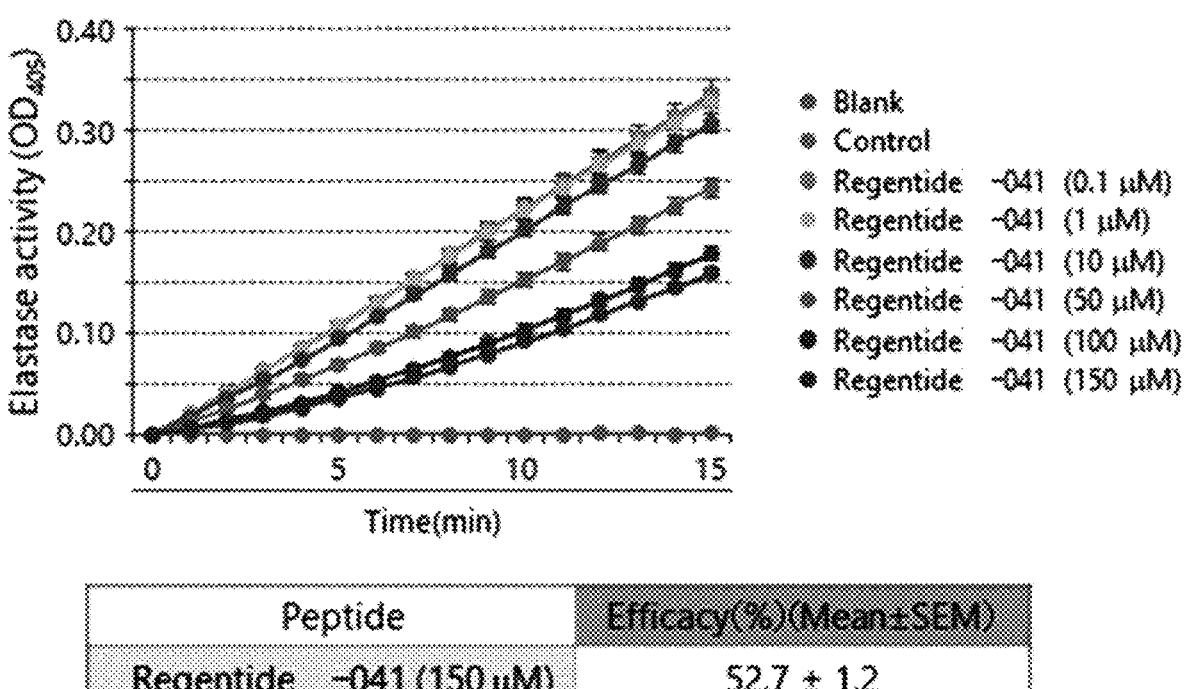
FIG. 4 is a view showing the results of analyzing the elastase activity inhibitory ability of Regentide-041 according to the present invention.

As shown in FIG. 4, it was confirmed that Regentide-041 increased the elastase activity inhibitory ability in a concentration-dependent manner, and had superior elastase activity inhibitory ability compared to the control group. More specifically, it was confirmed that the regentide-041 150 μM treatment group had an elastase activity inhibitory ability of 52.7±1.2%.

4-2. Elastin Biosynthesis Ability Analysis

In order to confirm the elastin biosynthesis ability of Regentide-041, CCD-986sk cells, which are human skin fibroblasts, were dispensed at $3 \times 10^5$ cells/well in a 6-well plate, and then cultured in cell culture conditions for 24 hours. Thereafter, the medium was removed, washed once using 1×DPBS, and then Regentide-041 was added to an FBS-free medium at various concentrations (0.1, 0.2, 0.5, and 1 μM) and further cultured for 24 hours. The medium cultured for each time period was recovered. The secretion amount of elastin secreted into the medium was measured for absorbance at 450 nm after treatment with Elastin ELISA Kit (Cusabio Biotech, Wuhan, China). The results of analyzing the elastin secretion amounts are shown in FIG. 5.

Figure 5:
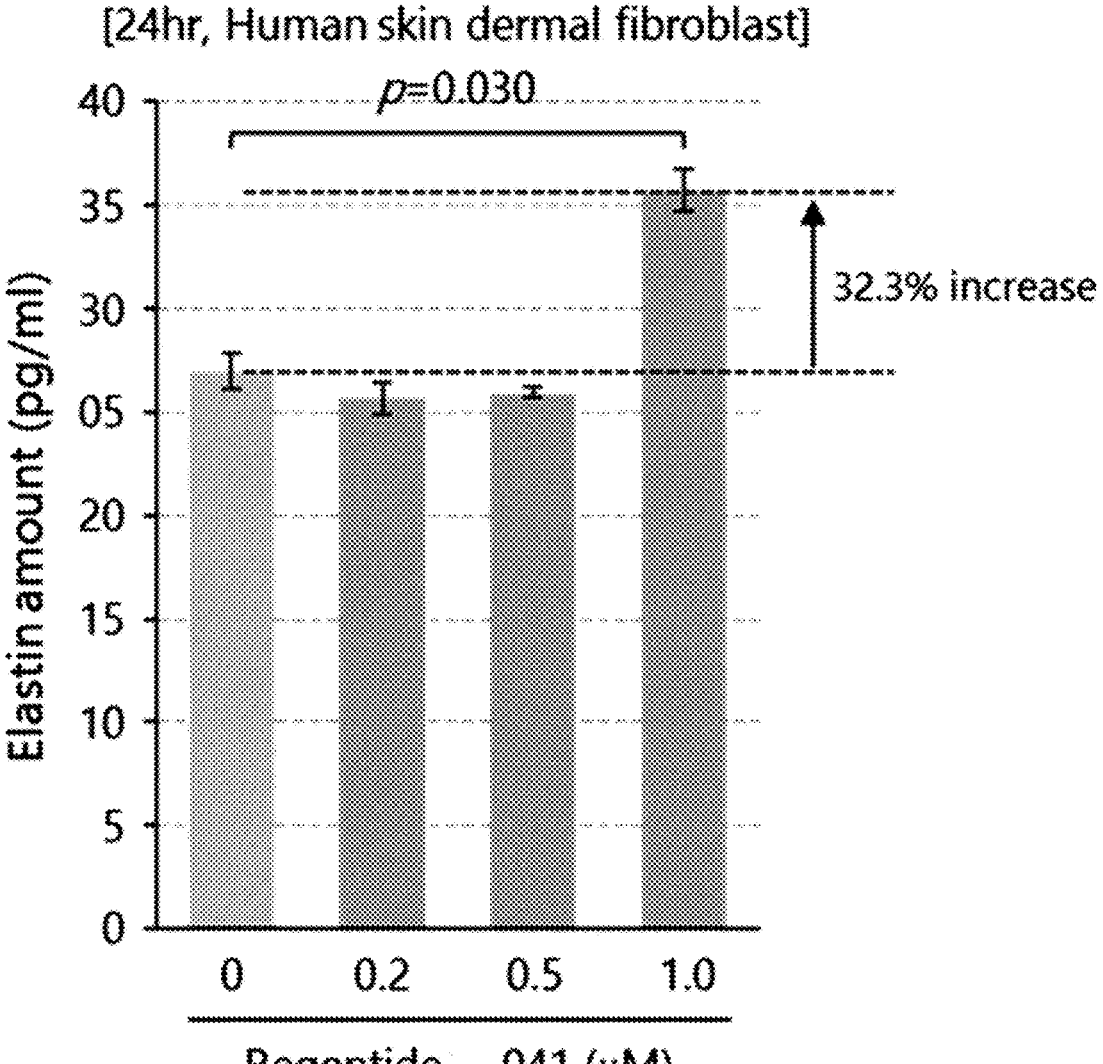
FIG. 5 is a view showing the results of analyzing the elastin biosynthesis ability of Regentide-041 according to the present invention.

As shown in FIG. 5, it was confirmed that the elastin biosynthesis ability of the Regentide-041 treatment group was increased. Particularly, it was confirmed that the amount of elastin was increased by 32.3% in the Regentide-041 1 μM treatment group compared to the control group.

Example 5. Confirmation of Wound Recovery Effect of Regentide-041

5-1. Confirmation of Wound Recovery Effect of Epidermal Keratinocytes

In order to confirm the wound recovery effect of Regentide-041, HaCaT cells, which are epidermal keratinocytes, were attached to a 6-well plate with an adhesive insert (Insert, Ibidi, Wisconsin, USA). The cells were dispensed at $6 \times 10^4$ cells/well in each well of the insert, and then cultured in cell culture conditions for 24 hours in a medium containing 2% FBS. Thereafter, the insert was removed and washed once using 1×DPBS. Regentide-041 was added to the medium at various concentrations (0, 1, and 2.5 μM) in an FBS-free medium, and cell images were photographed at 100 times using a microscope (Nikon Eclipse E100, Tokyo, Japan) after 16 and 40 hours. The photographed micrographs are shown in FIG. 6.

Figure 6:
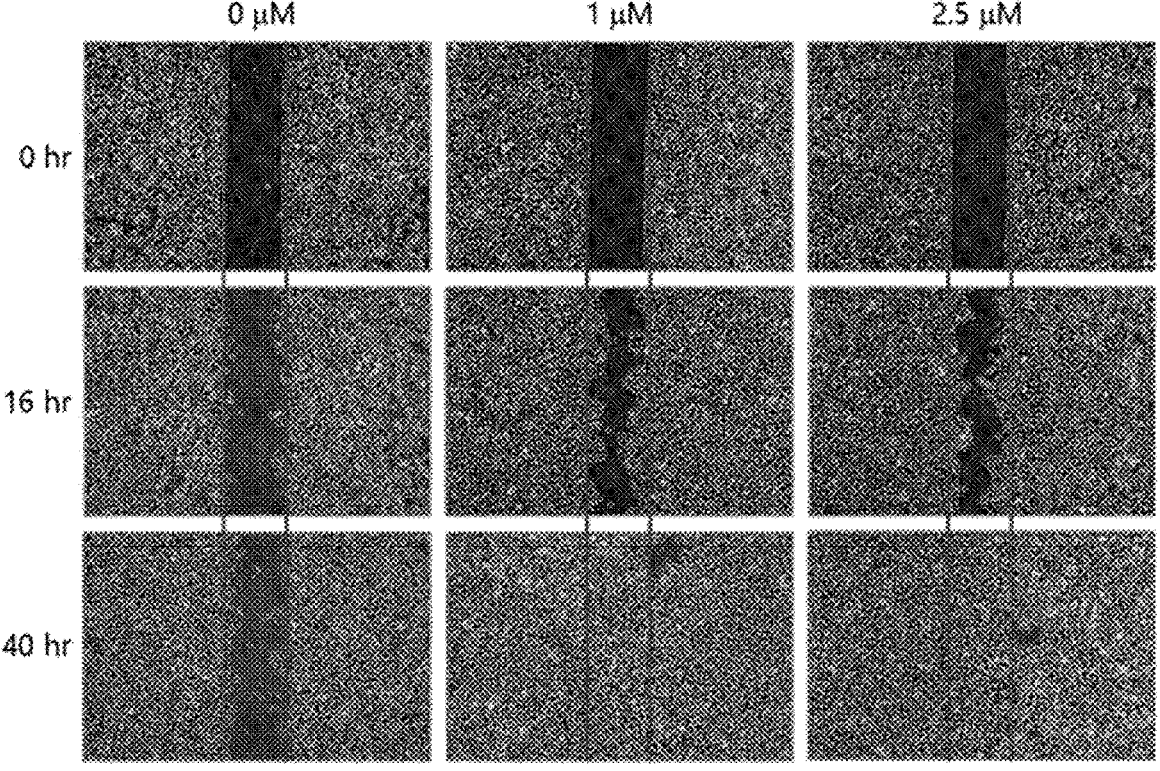
FIG. 6 is a view showing the results of confirming the epidermal keratinocyte migration promoting effect of Regentide-041 according to the present invention.

As shown in FIG. 6, it was confirmed that all of the groups treated with Regentide-041 increased the cell number and cell migration ability of epidermal keratinocytes.

5-2. Wound Recovery Promoting Effect of Fibroblasts

In order to confirm the wound recovery effect of Regentide-041, CCD-986sk, which is dermal cells, was attached to a 6-well plate with an adhesive insert (Insert, Ibidi, Wisconsin, USA). The cells were dispensed at $6 \times 10^4$ cells/well in each well of the insert, and then cultured in cell culture conditions for 24 hours in a medium containing 2% FBS. Thereafter, the insert was removed and washed once using 1×DPBS. Regentide-041 was added to the medium at various concentrations (0, 1, and 2.5 μM) in an FBS-free medium, and cell images were measured at 100 times using a microscope (Nikon Eclipse E100, Tokyo, Japan) after 16 and 40 hours. The photographed micrographs are shown in FIG. 7.

Figure 7:
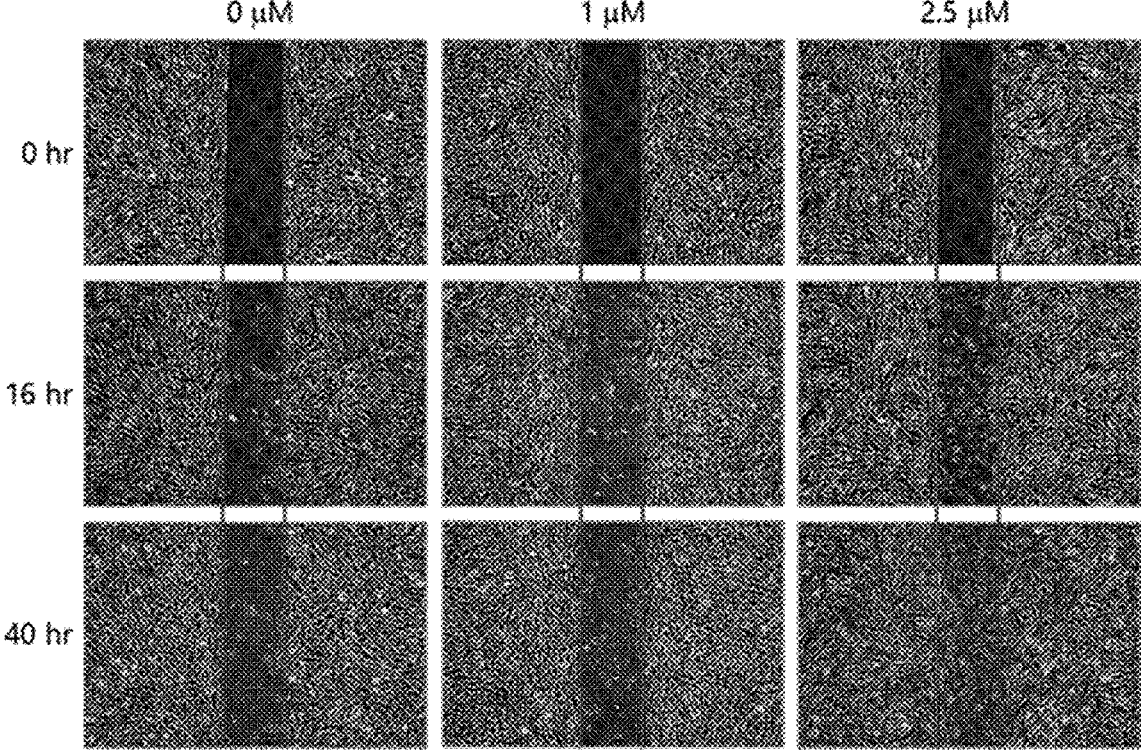
FIG. 7 is a view showing the results of confirming the fibroblast migration promoting effect of Regentide-041 according to the present invention.

As shown in FIG. 7, it was confirmed that all of the groups treated with Regentide-041 increased the cell number and cell migration ability of fibroblasts.

From the above results, since it is confirmed that Regentide-041 increases the cell number of skin cells and increases cell migration ability, this means that it may induce recovery of wounds such as cut wounds more rapidly.

Hereinafter, the present invention will be described in more detail through preparation examples. The preparation examples are only for illustrating the present invention, and the scope of the present invention is not to be construed as being limited by the preparation examples.

Preparation Example 1. Preparation of Cosmetic Preparation

1-1. Soft Lotion Manufacturing

A soft lotion was manufactured in a conventional manner by mixing 0.1% by weight of Regentide-041, 5.2% by weight of 1,3-butylene glycol, 1.5% by weight of oleyl alcohol, 3.2% by weight of ethanol, 3.2% by weight of polysorbate 20, 2.0% by weight of benzophenone-9, 1.0% by weight of carboxyl vinyl polymer, 3.5% by weight of glycerin, a trace amount of fragrance, a trace amount of preservative, and the remaining amount of purified water.

1-2. Milk Lotion Manufacturing

A milk lotion was manufactured in a conventional manner by mixing 0.1% by weight of Regentide-041, 5.1% by weight of glycerin, 4.2% by weight of propylene glycol, 3.0% by weight of tocopheryl acetate, 4.6% by weight of liquid paraffin, 1.0% by weight of triethanolamine, 3.1% by weight of squalane, 2.5% by weight of macadamia nut oil, 1.6% by weight of polysorbate 60, 1.6% by weight of sorbitan sesquioleate, 0.6% by weight of propylparaben, 1.5% by weight of carboxyl vinyl polymer, a trace amount of fragrance, a trace amount of preservative, and the remaining amount of purified water.

1-3. Nourishing Cream Manufacturing

A nourishing cream was manufactured in a conventional manner by mixing 0.5% by weight of Regentide-041, 4.0% by weight of glycerin, 3.5% by weight of petrolatum, 2.1% by weight of triethanolamine, 5.3% by weight of liquid paraffin, 3.0% by weight of squalane, 2.6% by weight of beeswax, 5.4% by weight of tocopheryl acetate, 3.2% by weight of polysorbate 60, 1.0% by weight of carboxyl vinyl polymer, 3.1% by weight of sorbitan sesquioleate, a trace amount of fragrance, a trace amount of preservative, and the remaining amount of purified water.

1-4. Massage Cream Manufacturing

A massage cream was manufactured in a conventional manner by mixing 0.5% by weight of Regentide-041, 4.0% by weight of glycerin, 3.5% by weight of petrolatum, 0.5% by weight of triethanolamine, 24.0% by weight of liquid paraffin, 3.0% by weight of squalane, 2.1% by weight of beeswax, 0.1% by weight of tocopheryl acetate, 2.4% by weight of polysorbate 60, 1.0% by weight of carboxyl vinyl polymer, 2.3% by weight of sorbitan sesquioleate, a trace amount of fragrance, a trace amount of preservative, and the remaining amount of purified water.

1-5. Manufacture of Body Cleanser for Cleaning

A body cleanser for cleaning was manufactured in a conventional manner by mixing 1 g of Regentide-041, 18 g of anionic surfactant, 5 g of nonionic surfactant, 7 g of glycerin, 3 g of sodium chloride, 1.5 g of natural olive liquid soap, 1 g of flavoring, and 100 g of water.

Hereinabove, a specific part of the present invention content has been described in detail, it is clear that this specific description is only a preferred embodiment to those skilled in the art, and the scope of the present invention is not limited thereby. Accordingly, it is intended that the substantial scope of the present invention be defined by the appended claims and their equivalents.

---

The invention claimed is:

1. A method for skin condition improvement, the method comprising a step of administering a composition comprising a peptide represented by the amino acid sequence of SEQ ID NO: 1, wherein the skin condition improvement is one or more kinds selected from the group consisting of skin aging improvement, skin regeneration, skin elasticity improvement, skin wrinkle prevention, skin wrinkle improvement, and skin wound regeneration.

2. The method of claim 1, wherein the skin aging is photoaging or natural aging.

3. The method of claim 1, wherein the peptide has a concentration of 0.1 to 1,000 µM.

4. The method of claim 1, wherein the composition is formulated into a filler.

5. The method of claim 1, wherein the composition is a cosmetic composition, food composition, or filler composition.

* * * * *

SEQUENCE LISTING

```
<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: Synthesized Peptide

<400> SEQUENCE: 1

Cys Ile Pro Arg Gly Gly Ile Cys Leu Val Ala Leu
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Regentide-041
<220> FEATURE:
<221> NAME/KEY: NON_TER
<222> LOCATION: (12)
<223> OTHER INFORMATION: amine group

<400> SEQUENCE: 2

Cys Ile Pro Arg Gly Gly Ile Cys Leu Val Ala Leu
1               5                   10
```